(12) United States Patent
Na

(10) Patent No.: US 12,262,940 B2
(45) Date of Patent: Apr. 1, 2025

(54) APPARATUS FOR TREATING SUBMUCOSAL TISSUE

(71) Applicant: VIOL CO. LTD., Seongnam-si (KR)

(72) Inventor: Jongju Na, Seoul (KR)

(73) Assignee: VIOL CO. LTD., Seongnam-si (KR)

( * ) Notice: Subject to any disclaimer, the term of this patent is extended or adjusted under 35 U.S.C. 154(b) by 363 days.

(21) Appl. No.: 16/969,614

(22) PCT Filed: Dec. 20, 2018

(86) PCT No.: PCT/KR2018/016355
§ 371 (c)(1),
(2) Date: Aug. 13, 2020

(87) PCT Pub. No.: WO2019/160235
PCT Pub. Date: Aug. 22, 2019

(65) Prior Publication Data
US 2021/0030464 A1    Feb. 4, 2021

(30) Foreign Application Priority Data

Feb. 14, 2018    (KR) .................. 10-2018-0018217

(51) Int. Cl.
*A61B 18/14*    (2006.01)
*A61B 18/00*    (2006.01)

(52) U.S. Cl.
CPC .................. *A61B 18/1485* (2013.01); *A61B 2018/00101* (2013.01); *A61B 2018/00107* (2013.01); *A61B 2018/00404* (2013.01); *A61B 2018/00559* (2013.01)

(58) Field of Classification Search
None
See application file for complete search history.

(56) References Cited

U.S. PATENT DOCUMENTS

| | | | |
|---|---|---|---|
| 6,091,995 A | | 7/2000 | Ingle et al. |
| 6,092,528 A | * | 7/2000 | Edwards ............ A61B 18/1206 606/41 |
| 7,160,294 B2 | | 1/2007 | Croft |
| 2003/0181897 A1 | | 9/2003 | Thomas et al. |

(Continued)

FOREIGN PATENT DOCUMENTS

| | | |
|---|---|---|
| JP | 2007-524426 | 8/2007 |
| JP | 2009-517102 | 4/2009 |

(Continued)

OTHER PUBLICATIONS

EPO, European Search Report of EP 18906219.3 dated Oct. 21, 2021.
SIPO, Office Action of CN 201880089485.2 dated Feb. 18, 2023.

*Primary Examiner* — Sean W Collins
*Assistant Examiner* — Nora W Rhodes
(74) *Attorney, Agent, or Firm* — LEX IP MEISTER, PLLC

(57) ABSTRACT

A submucosa treating apparatus according to an exemplary embodiment of the present invention includes: a probe that is capable of approaching mucosa of a treatment field; an electrode that is provided in the probe, and applies an electrical signal to blood vessels of submucosa; and a guide where the probe is movably accommodated, and a guide where the probe is movably accommodated, and guiding a position of the electrode with respect to the mucosa.

12 Claims, 16 Drawing Sheets

(56) References Cited

U.S. PATENT DOCUMENTS

| | | | |
|---|---|---|---|
| 2007/0233191 A1* | 10/2007 | Parmer | A61B 18/18 607/1 |
| 2009/0222060 A1* | 9/2009 | Boyd | A61N 1/36007 607/48 |
| 2012/0226271 A1 | 9/2012 | Callas et al. | |
| 2013/0245728 A1 | 9/2013 | Galen et al. | |
| 2014/0100557 A1 | 4/2014 | Bohner et al. | |
| 2015/0011993 A1 | 1/2015 | Horlle | |
| 2016/0121112 A1 | 5/2016 | Azar | |
| 2017/0071781 A1* | 3/2017 | Skalnyi | A61B 18/1485 |
| 2017/0143956 A1* | 5/2017 | Gregson | A61N 1/36007 |
| 2017/0252089 A1 | 9/2017 | Hester et al. | |
| 2018/0028267 A1 | 2/2018 | Onik et al. | |

FOREIGN PATENT DOCUMENTS

| | | |
|---|---|---|
| JP | 2009-538176 | 11/2009 |
| JP | 2012-24371 | 2/2012 |
| JP | 2012024371 A * | 2/2012 |
| JP | 2021-503359 | 2/2021 |
| KR | 10-2001-0067637 | 7/2001 |
| KR | 20-0272153 | 4/2002 |
| KR | 20080091107 | 10/2008 |
| KR | 10-2014-0144703 | 12/2014 |
| KR | 10-2017-0072379 | 6/2017 |

\* cited by examiner

APPARATUS FOR TREATING SUBMUCOSAL TISSUE

TECHNICAL FIELD

The present invention relates to an apparatus for treating submucosa. More particularly, the present invention relates to a submucosa treating apparatus that is used in treatment of blood vessels existing in the submucosa by using an electrical signal, thereby improving operation safety and convenience.

BACKGROUND ART

The body's mucosa refers to the inner wall of a hollow organ that is in direct contact with the outside, such as the respiratory, digestive, and urogenital organs. More specifically, mucosa of the body may be classified into oral mucosa, nasal mucosa, throat mucosa, bronchial mucosa, vaginal mucosa, glans mucosa, urethral mucosa, anal mucosa, and the like according to position.

Referring to FIG. 16, in general, the mucosa structure has a structure similar to that of the skin. The mucosa formed of epithelium exposed to the outside, and lamina propria corresponds to the epidermal layer of the skin, and the submucosa positioned below the mucosa corresponds to the dermal layer of the skin. That is, similar to the skin, there are numerous blood vessels in the submucosa, and these blood vessels are involved in the growth and synthesis of cellular and extracellular components present in the mucosa and submucosa.

Collagen is the most abundant protein in skin with good elasticity and mucosa, and provides the mechanical and structural integrity necessary to maintain its function. There are many types of collagen, and collagen I is the most common. There is a process called fibrillogenesis, which forms collagen fibers or is structured in the form of related fibrils. Other types of collagen include collagen III collagen IV, collagen VII and collagen VIII The second most important protein in the dermis is elastin. Elastin is composed of an insoluble elastic fiber with a central hydrophobic nucleus surrounded by a fibrous structure. Although elastin is a hydrophobic protein, but it is important in maintaining elasticity and skin resistance than collagen.

Such an extracellular connective tissue of the submucosa or dermis can be damaged as a result of an inflammation reaction. Aging, a dry environment, physical damage due to repeated friction, and exposure to chemical materials increase the inflammation reaction of mucosa and submucosa and activate the proteolytic system of the extracellular matrix. Phagocytes released into tissues through blood vessels cause inflammation and release matrix metalloproteinase (MMP). The MMP breaks down collagen and elastin molecules after the inflammation process. MMP-1 degrades collagen I and collagen III, while MMP-12 most actively degrades elastin. Excessive collagen and elastin breakdown leads to flaccidness and elongation of mucosa tissue.

Meanwhile, various diseases or abnormal symptoms may occur in mucosa, and an appropriate treatment should be performed according to the symptoms.

As one of the symptoms of mucosa abnormalities in the body, vaginal mucosa is loosened in women, which is vaginal relaxation. Vaginal mucosa in women is composed of tissues with good elasticity, but when sexual intercourse and childbirth are repeated, elasticity and friction are reduced and contractility is deteriorated as vaginal mucosa gradually loosens.

As such, when the contractility of vaginal mucosa is deteriorated, pressure and friction are reduced during sexual intercourse, and not only is sexual pleasure reduced, but also can be expanded to problems of incontinence or self-confidence, resulting in psychological atrophy. Therefore, treating or treating symptoms of relaxation becomes an important task.

The above information disclosed in this Background section is only for enhancement of understanding of the background of the invention, and therefore it may contain information that does not form the prior art that is already known in this country to a person of ordinary skill in the art.

DISCLOSURE

Technical Problem

Exemplary embodiments of the present invention provide a submucosa treating apparatus using an electrode that conducts an electrical signal so as to maintain mucosa tissue contractility and improve elasticity by normalizing abnormal hyperproliferation of the causal blood vessel through application of heat to blood vessels of submucosa that causes inflammation reactions that cause the breakdown of collagen and elastic molecules in mucosal tissue or loosening or exacerbation of vaginal mucosa.

In addition, the exemplary embodiments of the present invention provide a submucosa treating apparatus that can ensure safety of the treatment procedure of mucosa tissue, improve convenience of the procedure, accurately control the electrode position with respect to mucosa, and facilitate electrode position control.

In addition, the exemplary embodiments of the present invention provide a submucosa treating apparatus that can minimize damage and side effects of surrounding nerves or tissues of mucosa to be treated.

In addition, the exemplary embodiments of the present provide a submucosa treating apparatus that can shorten the time required for mucosa treatment and minimize patient discomfort.

Technical Solution

A submucosa treating apparatus according to an exemplary embodiment of the present invention includes: a probe that is capable of approaching mucosa of a treatment field; an electrode that is provided in the probe, and applies an electrical signal to blood vessels of submucosa; and a guide where the probe is movably accommodated, and guiding a position of the electrode with respect to the mucosa.

A position of the guide with respect to the mucosa may be fixed, and the probe may be rotatable with respect to the guide.

The guide may include a referential position mark, and may guide a rotation position of the electrode with respect to the mucosa with reference to the referential position mark.

The guide may include: a body portion where a first accommodation hole in which the probe is rotatably accommodated is formed; and an expanded portion of which the area of the cross-section expands as away from the body portion, communicating with the first accommodation hole, and where a second accommodation hole of which a diameter is larger than the head portion.

The probe may be straightly movable with respect to the guide.

The submucosa treating apparatus may further include: a guide portion for guiding rotation and straight-line movement of the probe with respect to the guide the guide, wherein the guide portion may include a guide groove formed in the probe, and a guide protrusion formed in the guide and sliding along the guide groove.

The guide groove may include: a linear guide groove that extends along a length direction of the probe at an outer surface of the probe; and a plurality of rotation guide grooves that communicate with the linear guide groove and are spaced apart from each other along the length direction of the probe, and wherein each of the plurality of rotation guide grooves may extend along a circumferential direction of the probe at the outer surface of the probe.

The plurality of rotation guide grooves may include first, second, and third rotation guide grooves that continuously neighbor each other, and the linear guide groove may include a first section guide groove formed between the first rotation guide groove and the second rotation guide groove, and a second section guide groove formed between the second rotation guide groove and the third rotation guide groove, and disposed on a line different from the line where the first section guide groove is disposed along the length direction of the probe.

The plurality of rotation guide grooves may be spaced apart from each other by as much as a length of the electrode along the length direction of the probe.

The submucosa treating apparatus may include a plurality of restraining grooves formed in the guide groove, and wherein the guide protrusion is accommodated while being position-fixed in the plurality of restraining grooves.

The plurality of restraining grooves may be formed in the rotation guide groove and spaced apart from each other along a circumferential direction of the probe.

The plurality of restraining grooves may be spaced from each other by as much as a length of the electrode along the circumferential direction of the probe.

A pair of cut-out portions may be formed along the length direction of the probe at an end of the body portion, and may be distanced from each other along the circumferential direction of the probe, and the guide protrusion may be disposed at a free end of a cantilever structure formed by the pair of cut-out portions.

The submucosa treating apparatus may include a position-mark formed in the probe, and indicating a position of the probe with respect to the guide.

The probe may include: a load portion; and a head portion that is formed at an end of the load portion, while having a size that is more expanded than the load portion, and where the electrode is mounted.

The electrode may be mounted to partially cover an outer surface of the head portion while having a size smaller than the head portion, and the outer surface of the electrode may be curved such that the electrical signal is emitted in a radial shape through the curved surface of the electrode.

The head portion may include a weight body thereinside.

The electrode may include: an electrode pad attached to the probe; and an electrode protrusion protruding from an outer surface of the electrode pad.

The submucosa treating apparatus may include a coating layer formed at the outer surface of the electrode, the coating layer suppressing thermal conduction to the mucosa from the electrode.

The electrical signal may be a pulse signal that is iteratively conducted while having at least one delay time.

Advantageous Effects

According to the exemplary embodiments of the present invention, it is possible to normalize abnormal hyperproliferation of the causal blood vessel by applying appropriate heat damage to the blood vessel of the submucosa, thereby maintaining the contractility of the mucosa tissue and improving elasticity in early stages.

In addition, it is possible to guarantee the safety of the mucosa treatment procedure and improve the convenience of the procedure.

In addition, the operator can directly check the position of the electrode with respect to mucosa, and can accurately control the position of the electrode with respect to mucosa.

In addition, it is possible to easily control the position of the electrode. In addition, it is possible to enable objective and professional treatment regardless of the experience and competence of the operator.

In addition, damage and side effects of surrounding nerves or tissues of the mucosa to be treated can be minimized.

In addition, it is possible to shorten the procedure time required for the mucosa treatment procedure, and to minimize side effects or patient discomfort after the procedure.

MODE FOR INVENTION

Figure 1:
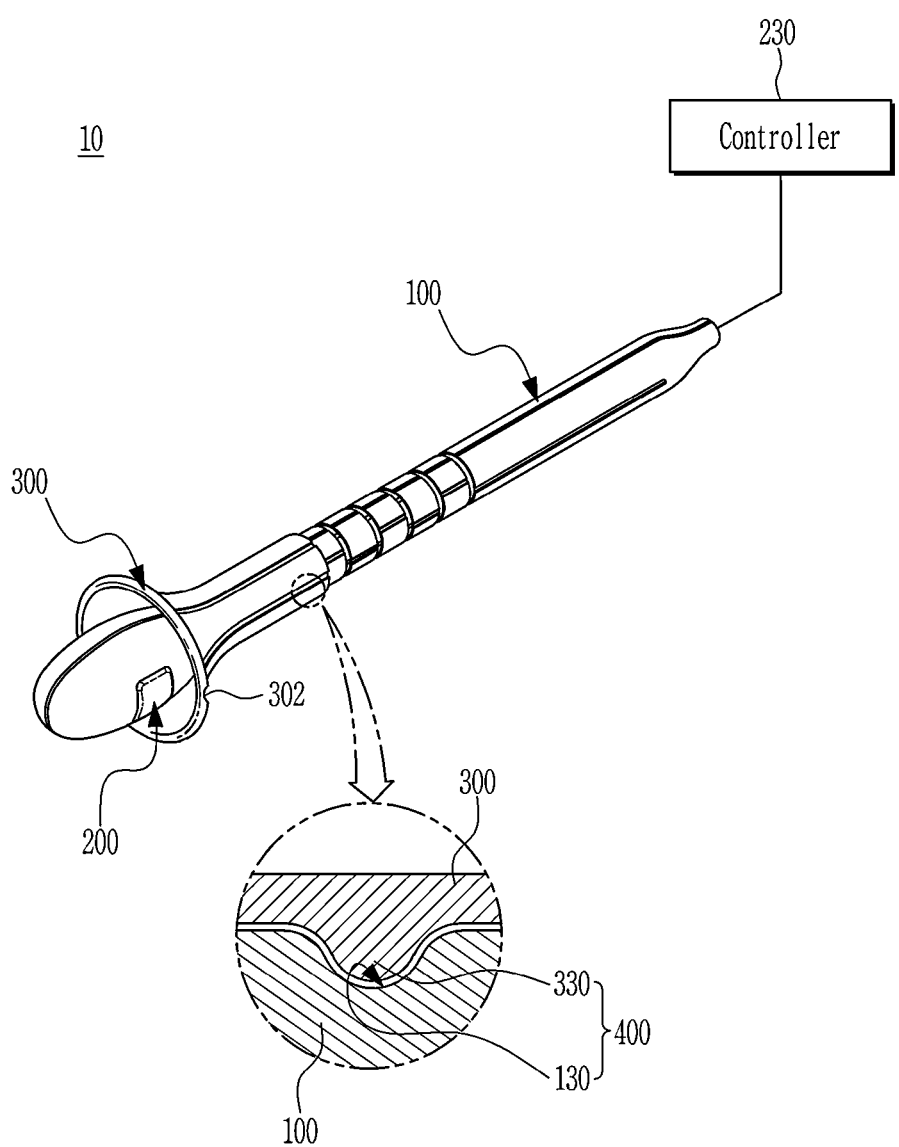
FIG. 1 is a perspective view of a submucosa treating apparatus according to an exemplary embodiment of the present invention.

In the following detailed description, only certain exemplary embodiments of the present invention have been shown and described, simply by way of illustration. As those skilled in the art would realize, the described embodiments may be modified in various different ways, all without departing from the scope of the present invention.

The drawings and description are to be regarded as illustrative in nature and not restrictive. Like reference numerals designate like elements throughout the specification.

In the present specification, it is to be understood that when one component is referred to as being "connected to" another component, it may be connected directly to another component or be connected indirectly to another component with the other component interposed therebetween. In addition, unless explicitly described to the contrary, the word "comprise" and variations such as "comprises" or "comprising" will be understood to imply the inclusion of stated elements but not the exclusion of any other elements.

It will be understood that when an element such as a layer, film, region, or substrate is referred to as being "on" another element, it can be directly on the other element or intervening elements may also be present. Throughout the specification, the word "on" means positioning on or below the object portion, but does not essentially mean positioning on the upper side of the object portion based on a gravitational direction.

Figure 2:
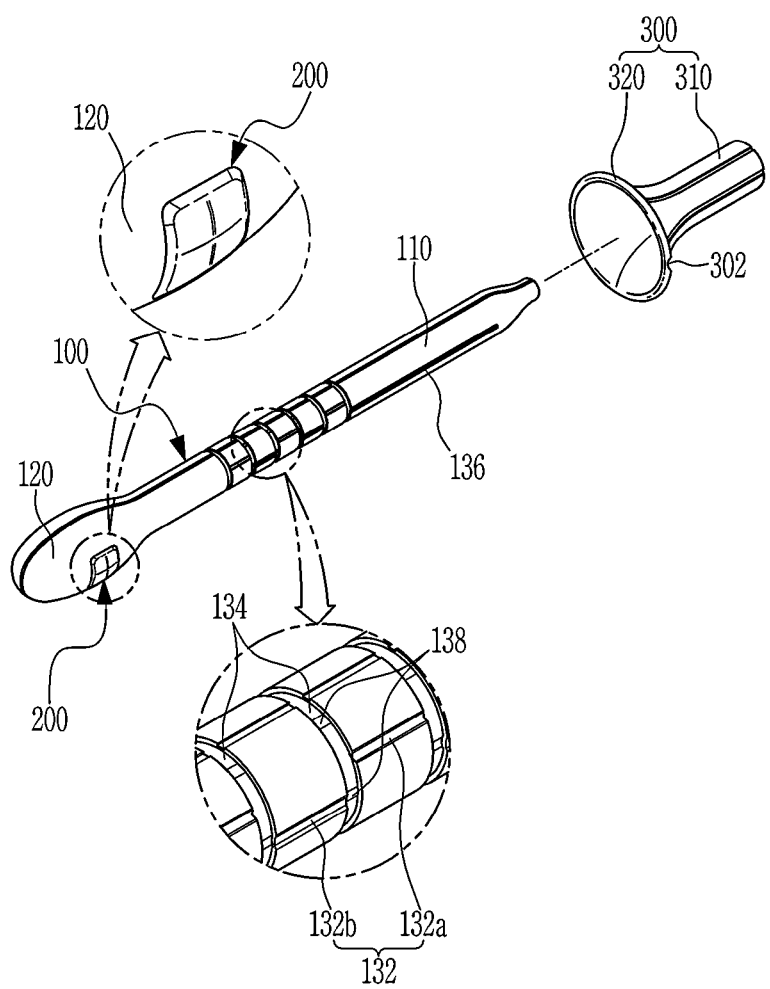
FIG. 2 is an exploded perspective view of the submucosa treating apparatus according to the exemplary embodiment of the present invention.

Referring to FIG. 1 and FIG. 2, a submucosa treating apparatus 10 according to an exemplary embodiment of the present invention includes a probe 100 that can approach mucosa of a treatment region, and an electrode 200 that is provided in the probe 100 and applies an electrical signal to a blood vessel of the submucosa. In addition, the submucosa treating apparatus 10 may further include a guide 300 where the probe 100 is movably accommodated, and guiding a position of the electrode 200 with respect to the mucosa.

The electrode 200 may have a curved external surface, and the electrical signal may be emitted in the radial shape through the curved surface.

The electrical signal applied to the electrode 200 may be a pulse signal that is repeatedly conducted with at least one delay time. Additionally, the guide 300 guides a position of the electrode 200 with respect to the mucosa.

For reference, in the present invention, mucosa is defined to include various types of mucosa of the body, which forms the inner wall of the hollow organ, which is in direct contact with the outside, such as respiratory organs, digestive organs, and genitourinary organs, and the present invention is not limited thereto.

More specifically, mucosa may be one of nasal mucosa, oral mucosa, prolapsed urethral mucosa, laryngopharyngeal mucosa, vaginal mucosa, glandular urethra mucosa, and anal mucosa.

For example, in case of vaginal mucosa, a dry environment, physical damage by repeated friction, and exposure to chemical materials increases mucosa's inflammatory process and decomposition of collagen and elastin molecules after increased inflammation, resulting in vaginal mucosa tissue relaxation and loosening.

In the case of blood vessels that cause or exacerbate the inflammation process, abnormal hyperproliferation of the cause blood vessels may be normalized when appropriate heat damage is applied. In addition, it is possible to maintain the contractility of vaginal mucosa and improve elasticity by reducing the number of new blood vessels excessively generated by physical damage.

An exemplary embodiment of the present invention can be provided to normalize abnormal hyperproliferation of the causal blood vessels, maintain contractility of vaginal mucosa, and improve elasticity. More specifically, an exemplary embodiment of the present invention is an apparatus that is capable of affecting submucosa by transmitting an electrical signal through the electrode into mucosa using a difference between each layer of mucosa tissue and tissue impedance, conductivity, and dielectric constant of each tissue, and can selectively treat blood vessels by using the characteristics of the blood vessel walls and blood vessels in which the impedance changes rapidly.

In addition, an exemplary embodiment of the present invention is a treating apparatus that can control the intensity of the electrical signal to be transmitted to control the degree of thermal reaction occurring in the blood vessel, and accordingly, a desired effect among congestion, regeneration, remodeling, growth, regrowth, degradation, and degeneration of blood vessel tissue can be selectively generated.

In addition, an exemplary embodiment of the present invention normalizes abnormal hyperproliferation by causing appropriate heat reaction in the blood vessel of the submucosa, which is a cause or exacerbation factor, induces phagocytosis or apoptosis of the blood vessel cells of the cause blood vessel, thereby increasing the therapeutic effect in each treatment purpose, reduces side effects caused by excessive heat damage to blood vessels and tissues in conventional therapy, and reduces the incidence of lesions due to hyperplasia remodeling of the removed blood vessels.

Specifically, a submucosa treating apparatus 10 according to an exemplary embodiment of the present invention is an apparatus that mainly treats blood vessels in submucosa by forming an electric field in the mucosa and submucosa.

That is, the submucosa treating apparatus 10 can treat various lesions by forming an electric field evenly in a certain region within mucosa and submucosa, thereby causing heat action in the blood vessel. Unlike conventional high-frequency therapy that heats the mucosa tissue itself with heat for the main purpose of collagen production in mucosa, the submucosa treating apparatus 10 uses a phenomenon that when an electric field of a specific condition is formed in a tissue, an electric signal is mainly applied to a blood vessel rather than a tissue other than a blood vessel.

In other words, the conventional high-frequency treatment technology requires a relatively long conduction time since collagen generation in mucosa is the main purpose, but the present invention can provide a therapeutic effect even with a shorter conduction time.

It may be necessary to control complex conditions such as voltages, power, and impedance in mucosa in addition to the conduction time. In addition, in the exemplary embodiment of the present invention, it is possible for the blood vessel to heat coagulate before other tissues in the mucosa are coagulated due to the high conductivity to the blood vessel, and the short conduction time, in which selective coagulation occurs in the blood vessel, usually means within 50 ms, more broadly within 100 ms, and more broadly within 300 ms.

Meanwhile, in the exemplary embodiment of the present invention, a plurality of pulse signals, which are electrical signals having a conduction time that is repeated one or more times with a certain delay time, may be generated to prevent excessive thermal reactions in mucosa tissue other than blood vessels and to concentrate thermal reactions in blood vessels.

That is, in the exemplary embodiment of the present invention, an applied voltage can be relatively increased by generating a repeated electrical signal with a delay time such that the conduction time can be formed relatively short, thereby minimizing the effect on surrounding tissues other than blood vessels.

In this case, one repeated conduction time may vary depending on various conditions of the apparatus, and duration of each conduction time may be the same or may be different. In addition, duration of the delay time may be different each time.

When the delay time is too short (e.g., less than 0.1 ms), heat damage may also occur in tissues other than causative blood vessels, and when the delay time is too long (e.g., over 500 ms), the continuity of the signal applied to the causative blood vessel is affected and thus the thermal reaction in the causative blood vessel may not be sufficiently achieved.

On the contrary, when the conduction time (electrical signal application time) is too long (e.g., over 450 ms), the excessive heat reaction may occur in tissues other than the blood vessel, and when too short (e.g., less than 1 ms), the thermal reaction in the blood vessel may not be sufficiently achieved.

Figure 15:
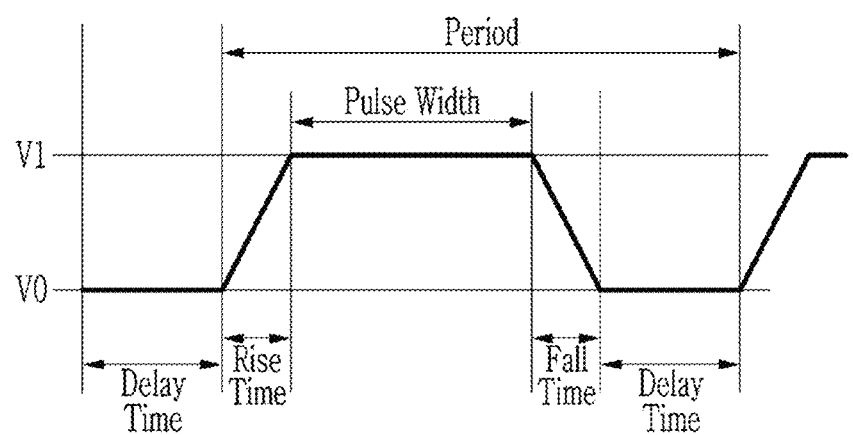
FIG. 15 is provided for description of a pulse signal that is iteratively conducted with a delay time in the submucosa treating apparatus according to the exemplary embodiment of the present invention.
Figure 16:
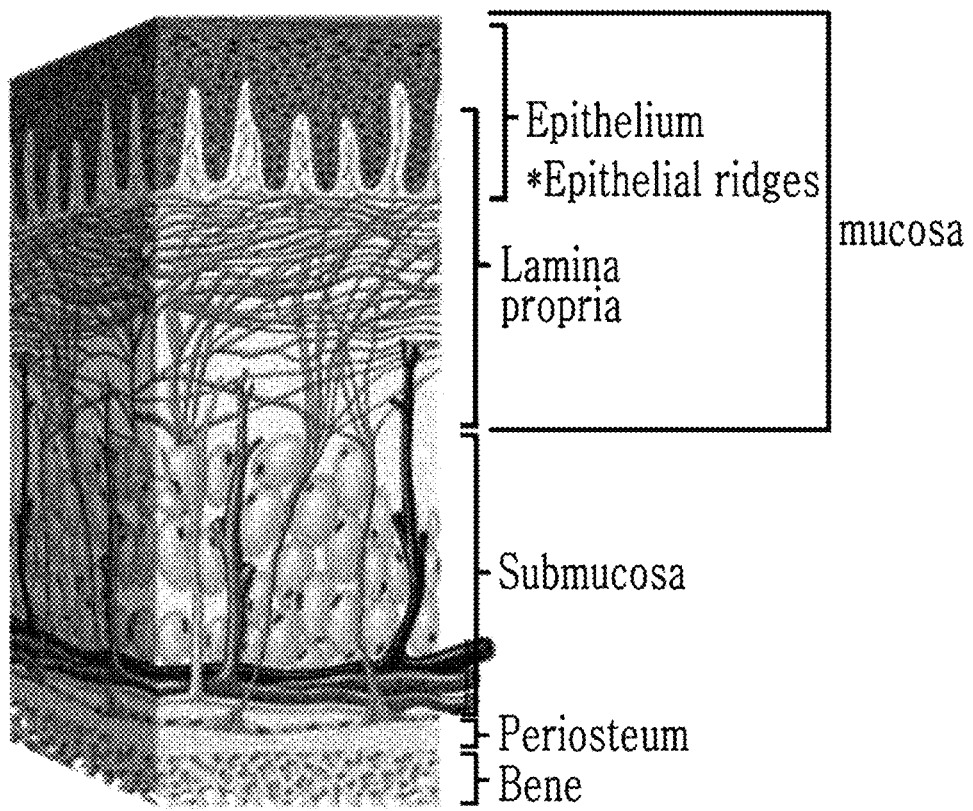
FIG. 16 is provided for exemplarily describing a general structure of mucosa.

In the exemplary embodiment of the present invention, an electrical signal applied to an electrode is a pulse signal as shown in FIG. 15, but it may be more preferable that the electrical signal is an AC pulse signal to cause more heat reaction than a DC pulse signal.

The technical principle of applying appropriate damage to blood vessel cells of a blood vessel through a treating apparatus according to an exemplary embodiment of the present invention is as follows.

Since most of the blood inside the causative blood vessel is composed of water and the conductivity is high, the electrical signal in the electric field is first attracted to the tissues in other mucosa first, and an impedance difference between blood vessel wall and blood is severe while the permittivity of the blood vessel wall is high, thereby causing thermal reaction by vibration of charge concentrated on the wall of the blood vessel. For reference, water molecules and ion materials cause vibration by an electromagnetic signal in the form of electromagnetic waves, and heat is generated by friction due to vibration.

In this case, due to the phenomenon that the electrical signal escapes through blood in an area in contact with an inner boundary of a blood vessel, less heat reaction occurs inside the wall of the blood vessel and heat is dispersed by the flowing blood, and thus an inner layer of the blood vessel wall has less thermal reaction and heat is concentrated in an outer layer of the blood vessel wall.

As described, the treatment apparatus according to the exemplary embodiment of the present invention is a treatment apparatus that can cause heat to the walls of blood vessels without damaging surrounding mucosa tissues other than the causal blood vessel tissue. Hereinafter, in the description, mucosa, which is a treatment target of a treating apparatus according to an exemplary embodiment of the present invention, is mainly described as an example of vaginal mucosa, but is not limited thereto.

As shown in FIG. 1 and FIG. 2, in an exemplary embodiment of the present invention, a probe 100 is provided to be selectively approachable to mucosa by manipulation of an operator. For example, the probe 100 is provided to be able to enter the body by manipulation of the operator.

More specifically, the probe 100 includes a load portion 110 and a head portion 120 formed at an end of the load portion 110 while having a more expanded size than the load portion 110.

As shown in FIG. 2, the load portion 110 may be formed in the shape of a rod having a predetermined length. For example, the load portion 110 may be a straight line-shaped rod having a circular cross-section, and alternatively, the load portion may be formed to have an oval or polygonal cross-sectional shape. As another example, the load portion may be formed in a bent shape, or two or more members may be combined to form a load portion.

The load portion 110 may have a length and a thickness which are sufficient for the operator to easily grip and manipulate, but the present invention is not limited by the length and the thickness of the rod portion 110.

Figure 9:
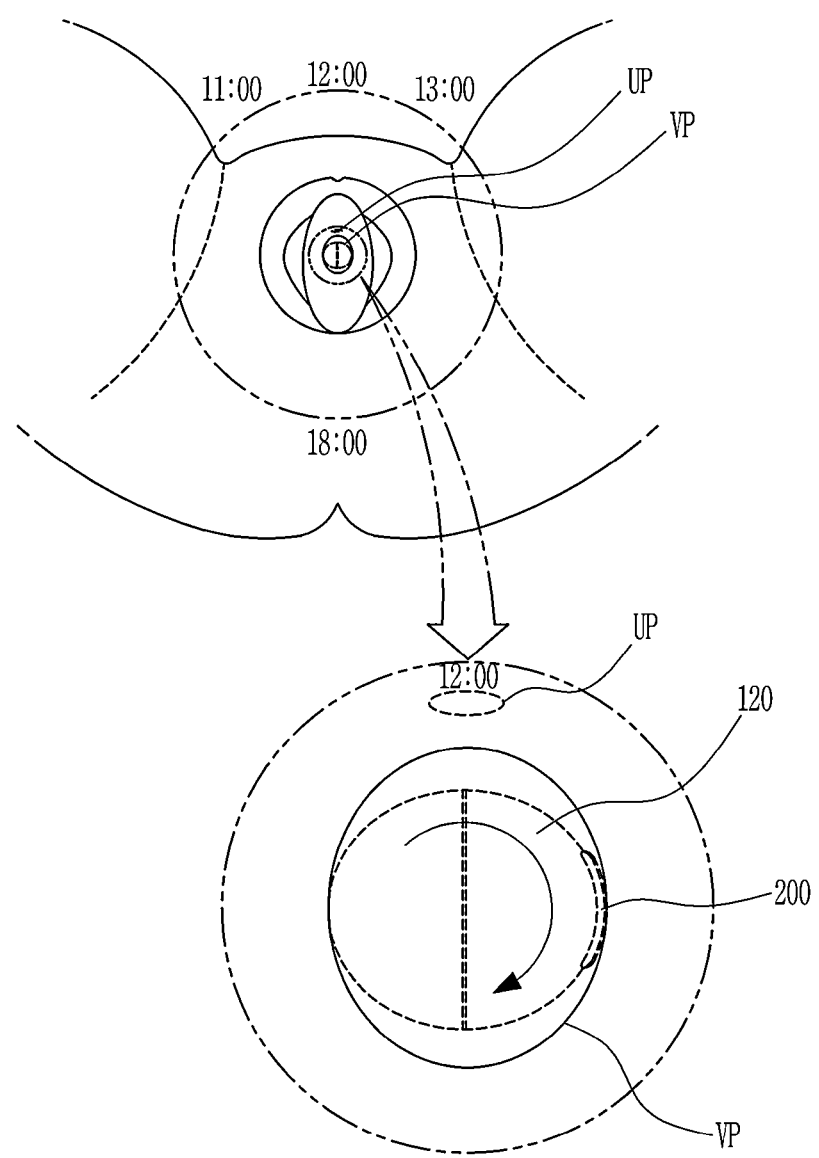
FIG. 9 to FIG. 11 are provided for description of a mucosa treatment process by the submucosa treating apparatus according to the exemplary embodiment of the present invention.
Figure 10:
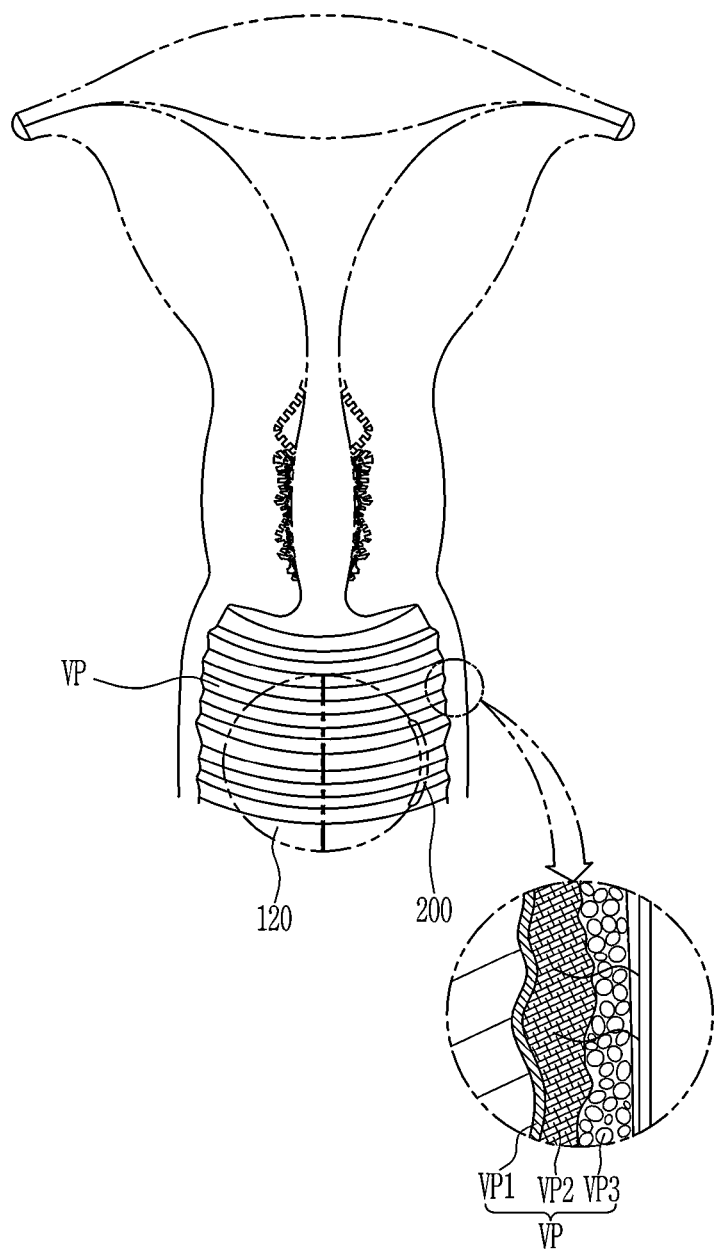

The head portion 120 is formed at the end of the load portion 110 such that the head portion 120 has a size that is more expanded than the rod portion 110, and the head portion 120 may enter the inside the body where mucosa is positioned, and for example, may enter the vagina and thus contact mucosa (refer to FIG. 9).

The shape and structure of the head portion 120 can be variously changed according to the required condition and design specifications. According to the exemplary embodiment of the present invention, an outer surface of the head portion 120 may be curved to minimize mucosa wounds when the head portion 120 is inserted into the body.

For example, the head portion 120 may be formed in the shape of an oval. As described, as the head portion 120 is formed in the shape of an oval that is similar to the body entrance, the head portion 120 can more easily enter the human body, and when the head portion 120 enters the inside of the body, the pressure applied to the patient is reduced, thereby obtaining a favorable effect that enables mucosa treatment in a more comfortable environment. Depending on cases, the head portion may be formed in the shape of a sphere, or may be formed in the shape of a mortar having a concave central portion, or other geometric shape.

For example, the average vaginal size (diameter) of women is around 35 mm and is relatively relaxed compared to other tissues, and thus a thickness of the head portion 120 is appropriately selected considering the vaginal size, but may be formed at 30 to 60 mm to facilitate adhesion to the inner wall of the vagina. In this case, a width of the head portion 120 during vaginal treatment may be preferably formed at 35 to 45 mm to optimize handling by the operator while reducing objections of a patient.

In addition, a grip portion (not shown) may be formed in the probe 100 such that the operator can easily grip the probe 100. In this case, the grip portion may be integrally formed with the probe 100 or selectively detachably coupled to the probe 100, and a mounting position of the grip portion may be variously changed according to the required condition and design specifications.

In addition, the probe 100 may be manufactured for a single use in consideration of patient hygiene. In addition, means (for example, anti-opening tags, software, RFID, sensors, stickers, etc.) and devices (for example, a visual alert device or audible alert device) for preventing repeated use of the probe 100, may be prepared together. In some cases, it may be possible to reuse the probe through sterilization or a sterilization process.

The electrode 200 is provided in the head portion 120 to apply an electrical signal while directly contacting mucosa (e.g., vaginal mucosa).

Here, when the electrode 200 is in contact with mucosa and applies an electrical signal, it may be defined as applying an electrical signal to blood vessels of submucosa to improve disease or abnormality of mucosa, and the present invention is not limited to the type or characteristic of the electrical signal.

For example, the electrode 200 may be formed to apply radio frequency (RF) energy to the vaginal mucosa. Depending on cases, the electrode may also be configured to apply other types of energy, such as microwaves or ultrasonic waves.

As the electrode 200, a conventional monopolar electrode 200 or bipolar electrode 200 may be used, and the present invention is not limited by the type of electrode 200.

The electrode 200 may be divided into two and thus may be formed as a pair, while disposing an insulator therebetween, or may be divided into two or more and thus a plurality of pairs may be formed, while disposing an insulator therebetween. In this case, one electrode operates as a (+) electrode and its neighboring electrode operates as a (−) electrode, thereby having bipolarity.

In addition, the electrical signal applied from the electrode 200 may be an AC electrical signal. The AC electrical signal has a characteristic that effectively induces a thermal coagulation reaction in blood vessels in the treated tissue.

Alternatively, the electrical signal applied from the electrode 200 may be a DC electrical signal. The DC electrical signal has a characteristic of helping to transfer materials such as drugs into the treatment tissue or destroying the tissue.

The electrical signal applied from the electrode 200 may have a frequency of 0.3 to 300 MHz. For example, the electrical signal applied from the electrode 200 may have a frequency of 0.5 to 10 MHz. Alternatively, the electrical signal applied from the electrode 200 may have a frequency of 0.5 to 3 MHz. As described, since the electrical signal applied from the electrode 200 has a frequency of 0.3 to 300 MHz, a proper heat reaction may be caused in the blood vessels of the submucosa, which are the cause or exacerbation of the inflammation process.

The blood vessels that cause or exacerbate the inflammation process are mostly new blood vessels (immature blood vessels), and the binding between cells constituting the blood vessel walls is looser than that of the normal blood vessels, and unlike normal blood vessels, it tends to be easily destroyed by relatively weaker electrical stimuli because the thickness of the blood vessel is thinner than that of the normal blood vessel and the cell structure of the blood vessel wall is weak.

In this case, a total amount of electrical signal energy applied from the electrode 200 may be predetermined to achieve a treatment purpose. More specifically, the intensity of the electrical signal that is conducted to the treatment tissue can be adjusted through a controller that receives a temperature or an impedance value of treatment tissue (e.g., epithelium tissue of vaginal mucosa or sub-mucosa tissue) as feedback, and thus it is possible to allow the total amount of predetermined electrical signal energy to be conducted to the treatment tissue in advance. For example, the total amount of the electrical signal energy may be set as a joule value or may be set as a conduction time.

For the reference, a temperature or impedance value of the treatment tissue may be measured by a temperature sensing line (or an impedance sensing line) connected to the electrode 200. For example, temperature sensing of the electrode 200 may be carried out at one point of the electrode 200. Depending on cases, it is also possible to sense temperatures of different points of the electrode to increase the accuracy of the electrode temperature measurement. In addition, impedance sensing of the treatment tissue may be carried by connecting a separate line to a point separate from the temperature sensing point of the electrode 200, or may be carried out by commonly using the temperature sensing line or an electrical signal conduction line. Likewise, the impedance sensing of the treatment tissue may be carried out at only one point or a plurality of points on the electrode 200.

For example, an impedance value measured through the impedance sensing may be set within a specific range for stable operation of the device. That is, when the impedance value of the tissue to be treated is excessively low, excessive current may flow and thus it may be dangerous, and on the contrary, when the impedance value of the tissue to be treated is excessively high, a very high voltage is required to apply an electrical signal, and thus it is necessary to set the impedance value suitable for use in any tissue. For example, skin and mucosa tissue connected to the skin, an electrical signal may be applied at a predetermined impedance predetermined range, which is set to 10 to 300Ω.

That is, the submucosa treating apparatus 10 according to the exemplary embodiment of the present invention may be formed for the operator to control an electrical signal under conditions that do not exceed a predetermined tissue temperature to thereby prevent side effects such as burns of the treated tissue and the like.

In addition, an emergency switch means may be provided to stop the operation of the device when a patient feels danger. In this case, after the operation of the apparatus is stopped by the emergency switch, the apparatus may be configured to operate again when the temperature of the tissue measured through a temperature feedback device falls below a certain temperature.

In addition, a target temperature of the treatment tissue may be set to 42° C. to 45° C. In this case, a temperature measured by the electrode 200 and an actual temperature measured at the treatment tissue may be different from each other, and the temperature of the electrode 200 may be higher by 3° C. to 5° C. than the temperature of the treatment tissue. In addition, a surface temperature (e.g., epithelium) of the treatment tissue may be different from that of the core (e.g., sub-mucosa), and thus the target temperature of the treatment tissue further includes that the core temperature is 42° C. to 45° C. Meanwhile, the shape and the size of the electrode 200 may be variously changed depending on required conditions and design specifications.

For example, the electrode 200 may be formed in the form of a plate protruded on the outer surface of the head portion 120. In this case, the electrode 200 may have a curved outer surface, and in this case, the outer surface of the electrode 200 may be formed to be curved corresponding to the curved outer surface of the head portion 120. For example, it may be formed of a portion of the sphere, that is, a curved surface corresponding to a portion of the outer surface of the sphere. As another example, it may be formed of a curved surface corresponding to a portion of the outer surface of the ellipsoid.

Figure 3:
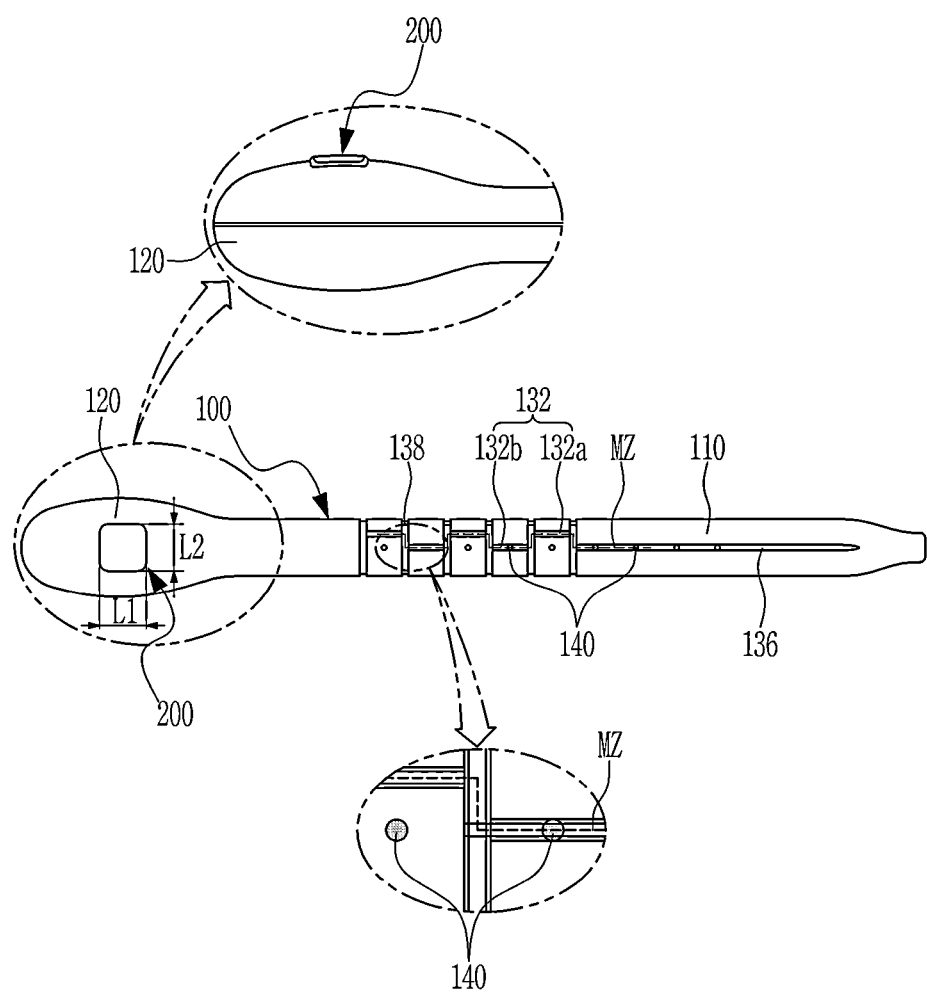
FIG. 3 and FIG. 4 are provided for description of a probe of the submucosa treating apparatus according to the exemplary embodiment of the present invention.

As shown in FIG. 2, FIG. 3, and FIG. 9, the outer surface of the electrode 200 is curved such that an electrical signal can be evenly emitted radially with reference to a center point of the curved surface to form an electric field in a wider area, the wound of mucosa due to the contact between the electrode 200 and mucosa can be minimized, and the contact efficiency (i.e., the efficiency to be sufficiently contacted) between the electrode 200 and mucosa can be increased.

Meanwhile, depending on cases, it is also possible to form the electrode in a concave recessed shape on the outer surface of the head portion. In the structure in which the electrode is formed in a concave form, a vacuum pressure for adsorbing mucosa on the outer surface of the electrode can be applied between the outer surface of the electrode and mucosa.

In the exemplary embodiment of the present invention, the electrode 200 is formed to be smaller than the head portion 120 in size and may be mounted to partially cover the outer surface of the head portion 120. For the reference, in the exemplary embodiment of the present invention, only one electrode 200 is provided in the head portion 120, but this is not restrictive, and a plurality of electrodes may be provided in the head portion. The electrode 200 may be formed of a material having excellent electrical conductivity and excellent thermal conductivity, and the material of electrode 200 may be variously changed according to required conditions. For example, the electrode 200 may be formed of stainless steel, copper, aluminum, gold, silver, and the like.

Figure 12:
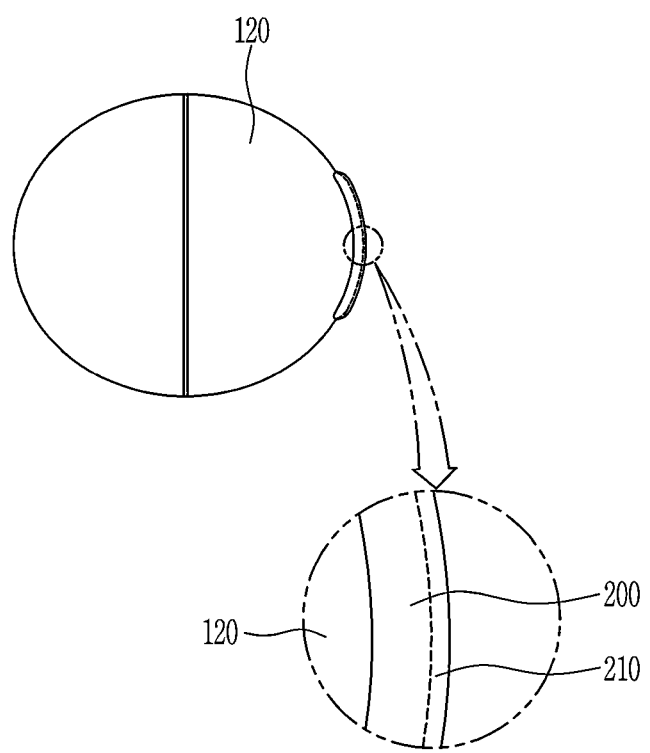
FIG. 12 and FIG. 13 are provided for description of another exemplary embodiment of an electrode in the submucosa treating apparatus according to the exemplary embodiment of the present invention.

Also, referring to FIG. 12, a coating layer 210 may be formed on the outer surface of electrode 200 to suppress the heat conduction from the electrode 200 to mucosa. This is to prevent rapid temperature rise of the mucosa surface due to direct contact between the electrode 200 and mucosa, and to reduce patient pain due to temperature rise of the mucosa surface.

That is, when the electrode 200 is in direct contact with the mucous membrane, the patient may feel pain due to an increase in the temperature of the mucosal surface even though the temperature of the submucosa has not reached the target temperature.

However, in the exemplary embodiment of the present invention, the coating layer 210 is provided between the electrode 200 and the mucosa surface such that the temperature of the submucosa may increase to the target temperature while preventing rapid temperature rise at the mucosa surface, thereby achieving an advantageous effect of minimizing patient's pain during mucosa treatment. Moreover, since the treatment time can be increased while minimizing the pain of the patient, an advantageous effect of further increasing the treatment effect can be obtained.

Various materials having low thermal conductivity and capable of application of an electrical signal may be used to form the coating layer 210, but the present invention is not limited by a material of the coating layer 210. For example, the coating layer 210 may be formed of one of silicon, polyurethane, paper, Nylone, and the like, or a combination thereof. Preferably, the coating layer 210 may be formed of a very thin thickness (e.g., 0.1 to 5 mm) through which an electrical signal applied from the electrode 200 is permeable. It is known that the maximum depth of heat reaction caused by an electrical signal conducted to a deep portion of the treatment tissue is usually ½ of the maximum length of the electrode 200. Thus, the electrode 200 may be formed in the form of the same quadrangle in the horizontal and vertical lengths so that a uniform therapeutic effect can be exhibited even though any part of the electrode 200 contacts the treatment site. In addition, the electrode 200 may have rounded edges (round shape) to prevent an edge effect in which thermal reaction is concentrated at the edge.

The size of the electrode 200 may be appropriately selected depending on a treatment tissue type and a targeted treatment depth, but the horizontal and vertical lengths of the electrode 200 are formed identically such that the area between the electrode 200 and the human body can be as large as possible.

As described, when the horizontal length and the vertical length of the electrode 200 are identically formed, resistance at the surface of the electrode 200 can be minimized and thus the temperature rise at the treatment tissue surface can be minimized, thereby minimizing the side effect such as burning and maximizing thermal reaction at the blood vessel of the treatment tissue.

For example, in the exemplary embodiment of the present invention, when the submucosa treating apparatus 10 is used for blood vessel treatment of vaginal submucosa, the electrode 200 may have a horizontal length or a vertical length of 15 to 20 mm.

As described, when the horizontal length and the vertical length of the electrode 200 are set to 15 to 20 mm, the thermal reaction region acting on the blood vessel can be evenly formed throughout the submucosa because the thickness from the vaginal mucosa surface to the deep layer of the vaginal submucosa is 7 to 10 mm, and as the size of the electrode is not too excessive, a temperature sensing line (thermo coupler) attached to the electrode 200 can evenly reflect the temperature of the entire electrode 200. More preferably, the horizontal or vertical length of electrode 200 may be 16 to 18 mm.

The thickness of the electrode 200 may be formed to be 0.1 to 0.5 mm. When the thickness of the electrode 200 is greater than 0.5 mm, a difference between the temperature of the treatment tissue and the temperature of the electrode 200 is increased, and a difference between a temperature at a portion where the temperature sensing line is attached to the electrode 200 and a temperature of a portion that is away from the temperature sensing line is increased. In addition, when the thickness of the electrode 200 is smaller than 0.1 mm, there is a possibility that the electrode 200 is deformed by the pressure applied to the electrode 200 by the treatment tissue during mucosa treatment, and the treatment safety is deteriorated. Thus, the thickness of the electrode 200 is appropriate to be 0.1 to 0.5 mm, and preferably may be 0.2 to 0.4 mm. Depending on cases, the horizontal and vertical lengths of the electrodes may be elongated, and even in this case, the electrode may be formed in a curved shape in both horizontal and vertical directions.

Figure 13:
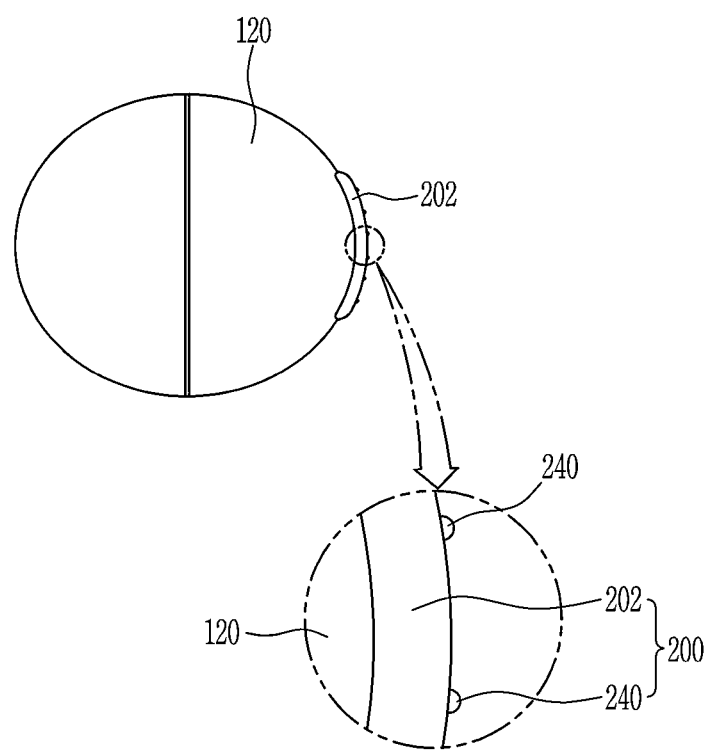

Meanwhile, referring to FIG. 13, according to another exemplary embodiment of the present invention, an electrode 200 may include an electrode 202 closely attached to a probe 100 and electrode protrusions 204 formed protruded from an outer surface of the electrode pad 202.

As described, the electrode protrusions 204 protrude from the outer surface of the electrode pad 202 and thus application of an electrical signal can be concentrated to the electrode protrusions 204 such that the treatment tissue can be treated intensively only in a local area to shorten the recovery period and reduce the side effects such as burns.

The electrode protrusion 204 may be formed in a hemisphere shape or a pointed column shape according to the required condition and design specifications, but the present invention is not limited by the shape of the electrode protrusion 204.

Meanwhile, an electrical signal generator (not shown) is connected to the probe 100 through a connector, and a main body portion (not shown) where the electrical signal generator is provided may be provided with a power supply and a central processing unit (CPU) that controls a temperature, impedance, electrical signal intensity, and the like.

In addition, the main body portion may be provided with a temperature sensing device, an impedance sensing device, and an operating device or a software program that converts measured values of the temperature sensing device and the impedance sensing device.

In addition, the main body portion may be provided with a user interface in which the operator sets a target treatment temperature, target treatment time, or target electric signal energy in advance. The user interface can display a temperature of the electrode 200 or a treatment tissue temperature, or the impedance of the treatment tissue, in real time. This helps a diagnosis function that allows the operator to estimate the treatment energy according to the impedance value of each treatment tissue.

For example, it is desirable to treat for a short time with a high electrical signal output when the impedance of the treatment tissue is low, and it is advantageous for effective treatment to treat for a long time with a low electrical signal output for a high treatment tissue impedance to prevent burns on the treatment surface.

A guide 300 is provided to guide a position of the electrode 200 with respect to the treatment field mucosa.

Here, guiding the position of the electrode 200 with respect to the treatment field mucosa is defined as identifying or specifying to the operator where the electrode 200 is positioned relative to the mucosa.

This is to ensure the safety of the blood vessel treatment procedure of the submucosa, and to improve the convenience of the procedure.

That is, when there is no means for guiding a position of the electrode 200 with respect to mucosa of the treatment field, the operator cannot precisely recognize the position of the electrode 200 inserted into the human body and thus it is difficult to uniformly treat the entire mucosa area, and objective treatment may be difficult because it is highly dependent on the operator's experience and competency due to the characteristic of the procedure.

For example, when the submucosa treating apparatus 10 of the exemplary embodiment of the present invention is used in vaginal submucosa treatment, position of the electrode 200 inserted into the vagina needs to be precisely controlled. Otherwise, a problem may occur in the peripheral nerves or tissues adjacent to vaginal mucosa, such as thermal burns or tissue stenosis.

In particular, when deep heat is applied to the vaginal mucosa between 11 o'clock and 1 o'clock directions based on the 12 o'clock position where the urethra is positioned along the circumferential direction of the vagina, irreversible side effects such as urethral stenosis may occur.

However, in the exemplary embodiment of the present invention, the position of the electrode 200 can be guided by the guide 300 and thus the position of the electrode 200 can be controlled such that the treatment effect can be optimized while minimizing the damage and side effects of the surrounding nerves or tissues of the mucosa being treated.

In addition, since it is possible to perform mucosa treatment while accurately recognizing the position of electrode 200, an advantageous effect that enables objective and professional treatment regardless of the operator's experience and competence can be obtained.

According to the exemplary embodiment of the present invention, the guide 300 is fixedly positioned relative to mucosa, and the probe 100 can be selectively rotatably accommodated in the guide 300. FIG. 9 illustrates the guide 300 that is provided in a fixed manner and used in the vagina, and the probe 100 provided rotatably according to the exemplary embodiment of the present invention.

As described, the position of the guide 300 is fixed with respect to the mucosa and the probe 300 rotates with respect to the guide 300 such that the operator can recognize the position of the electrode 200 with reference to the guide 300 even though the electrode 200 mounted to the probe 100 is hidden by being inserted into the vagina.

Figure 5:
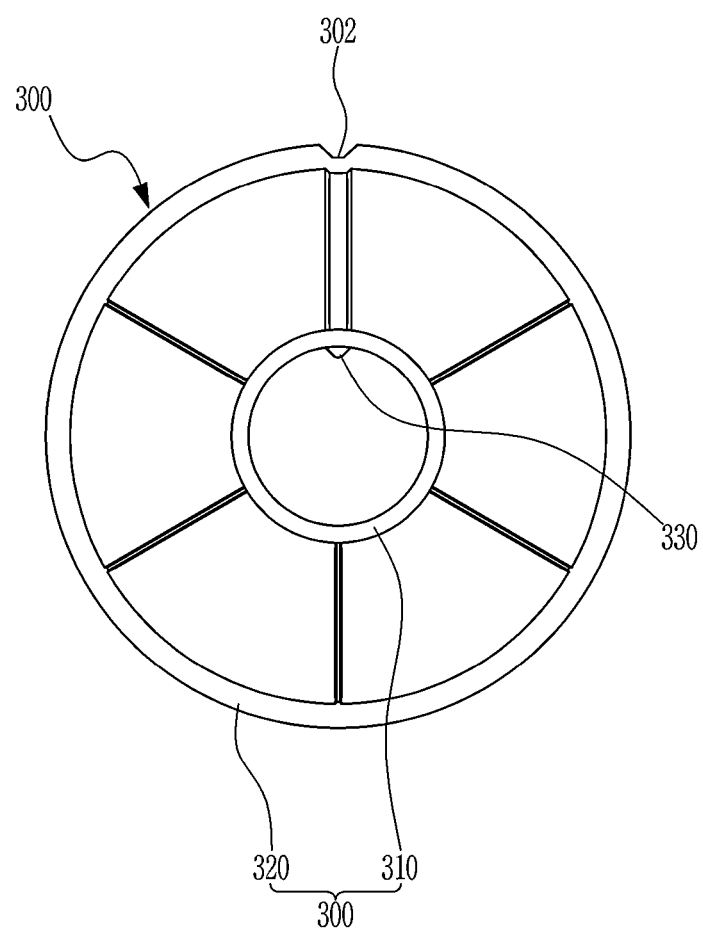
FIG. 5 and FIG. 6 are provided for description of a guide of the submucosa treating apparatus according to the exemplary embodiment of the present invention.

As shown in FIG. 5, according to the exemplary embodiment of the present invention, a referential position mark 302 is formed in the guide 300, and a rotation position of the electrode 200 with respect to mucosa can be controlled with reference to the referential position mark 302.

The referential position mark 302 may be formed in a protrusion shape or a recessed groove shape on the outer surface of the guide 300. Alternatively, the referential position mark may be marked or painted in a line form or a dot form. Hereinafter, an example where only one referential position mark 302 is formed in a recessed groove shape will be described. However, the present invention is not limited thereto, and a plurality of referential position marks may be formed on the guide.

For example, the guide 300 and the probe 100 are disposed to place the referential position mark 302 and the electrode 200 at the 12 o'clock direction, and the electrode 200 mounted to the probe 100 is inserted into the vagina while the guide 300 is fixed to the outside the vagina. Then, the operator can precisely recognize an exact position of the electrode 200 at the vaginal mucosa with reference to the referential position mark 302.

Figure 6:
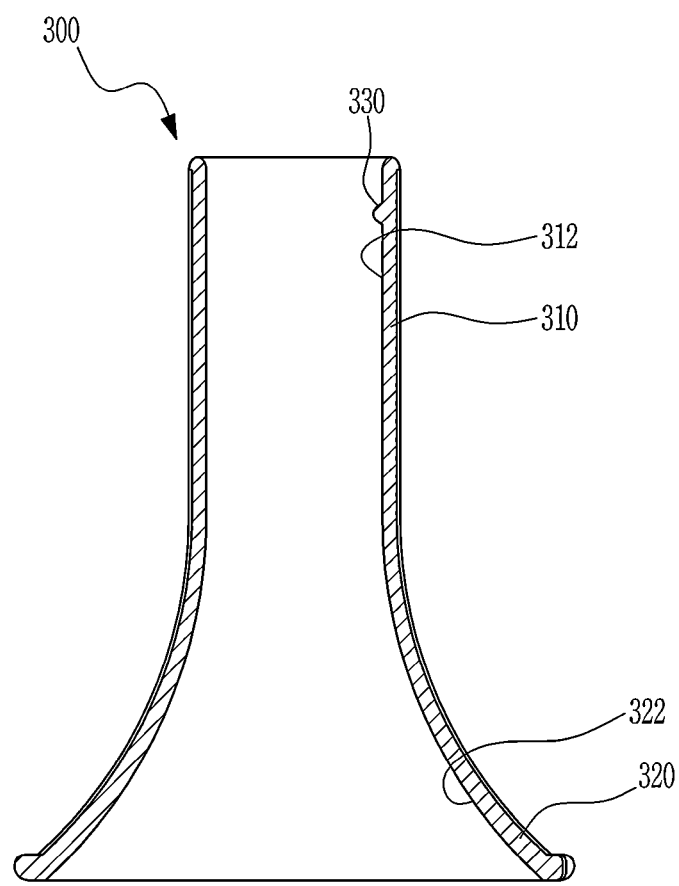

Meanwhile, as shown in FIG. 6, the guide 300 may include a guide main body portion 310 where a first accommodation hole 312 where the probe 100 is rotatably accommodated, and an expanded portion 320 where a second accommodation hole 322 connected with the first accommodation hole 312 and where the probe 100 is rotatably accommodated and formed while integrally expanded to the guide main body 310.

For example, the expanded portion 320 may have a cross-section that expands toward a distal end from a proximal end that is adjacent to the body portion 310.

That is, the expanded portion 320 may have a shape of which a diameter of the second accommodation hole 322 is increased going away from the body portion 310. For example, the expanded portion 320 may have a cross-section that is gradually expanded from one end to the other end like a trumpet.

In this case, the cross-section of the expanded portion 320 may have a circular, polygonal, or elliptical shape, and the present invention is not limited by the shape and structure of the expanded portion 320. For example, the expanded portion 320 may be formed in a size that can be fixed outside the vaginal inlet (a size that can be caught outside the vaginal inlet).

As described, the guide 300 not only enables the operator to recognize the position of the electrode 200 relative to mucosa, but also allows the electrode 200 to be accurately positioned in the target tissue to be treated and minimizes the movement of electrode 200 during treatment.

In addition, the probe 100 rotates with respect to the guide 300 while being inserted into the guide 300, and simultaneously, straightly moves along an axial line direction (i.e., a direction in which the first accommodation hole 312 is formed) of the guide 300. Thus, the electrode 200 can move (rotate) along the circumferential direction inside the vagina and move (straight line movement) along the length direction inside the vagina.

Meanwhile, referring back to FIG. 1, the submucosa treating apparatus 10 according to the exemplary embodiment of the present invention may include a guide portion 400 that guides rotation and straight line movement of the probe 100 with respect to the guide 300.

Here, guiding the straight line movement of the probe 100 with respect to the guide 300 is defined as suppressing the movement of the probe 100 that is dislocated from the straight line movement while the probe 100 moves along the straight line path with respect to the guide 300 and guiding the probe 100 to move only along the straight line path.

In addition, guiding the rotation of the probe 100 with respect to the guide 300 is defined as suppressing a rotation center of the probe 100 with respect to the guide 300 from being mislocated, and constantly maintaining the rotation center of the probe 100.

The guide portion 400 may be configured to guide rotation and straight line movement of the probe 100 relative to the guide 300 in various ways according to the required condition and design specifications.

For example, referring to FIG. 1, the guide portion 400 may include a guide groove 130 formed in the probe 100, and a guide protrusion 330 formed in the guide 30 to be movable along the guide groove 130.

While the guide protrusion 330 is accommodated in the guide groove 130, the movement of the guide protrusion 300 to the outside of the guide groove 130 is suppressed, and accordingly, rotation and straight line movement of the probe 100 with respect to the guide 300 can be guided.

In addition, as shown in FIG. 2, the probe 100 may be formed with an ingress groove 136 in communication with the guide groove 130, and the guide protrusion 330 enters the guide groove 130 through the ingress groove 136. For example, the ingress groove 136 may be formed in a straight line shape along the length direction of the probe 100. Depending on cases, it is also possible to form an ingress groove in the form of a curved line or inclined with respect to the length direction of the probe.

Referring to FIG. 2 and FIG. 3, in the exemplary embodiment of the present invention, the guide groove 130 may include a straight-line guide groove 132 formed at an outer surface of the probe 100 along the length direction of the probe 100, and a rotation guide groove 134 formed at the outer surface of the probe 100 along a circumferential direction of the probe 100 while being in communication with the straight-line guide groove 132.

Accordingly, when the guide protrusion 330 moves along the linear guide groove 132, straight line movement of the probe 100 with respect to the guide 300 is guided, and when the guide protrusion 330 moves along the rotation guide groove 134, rotation of the probe 100 with respect to the guide 300 is guided.

According to the exemplary embodiment of the present invention, the rotation guide groove 134 is provided in plural with intervals along the length direction of the probe 100, and each of the plurality of rotation guide grooves 134 may communicate with the linear guide groove 132. In this case, the plurality of rotation guide grooves 134 may be distanced as much as a length (i.e., as much as L1 in FIG. 3) according to the length direction of the probe 100. That is, the plurality of rotation guide grooves 134 may be formed to be spaced apart from each other by using the length (L1 of FIG. 3) of the electrode 200 along the length direction of the probe 100 as a separation pitch (P2 of FIG. 11).

Figure 11:
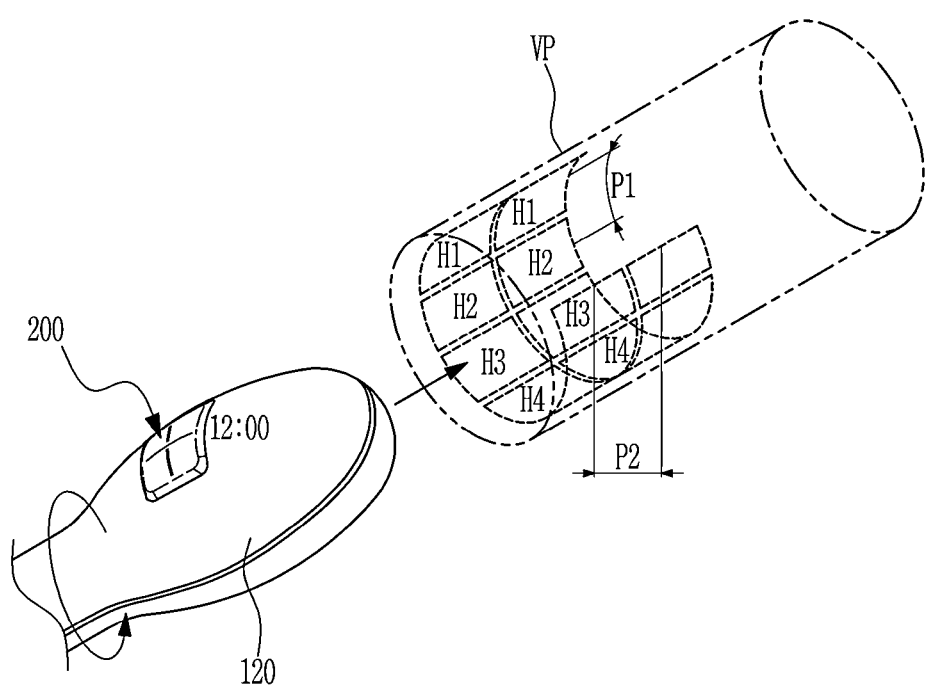

As described, the plurality of rotation guide grooves 134 are formed at a distance from each other by using the length (L1 of FIG. 3) of the electrode 200 along the length direction of the probe 100 as the separation pitch (P2 of FIG. 11), and the guide protrusions 330 pass through the respective rotation guide grooves 134 stepwisely such that when treatment according to the length direction of mucosa (e.g., H1→H1' or H2→H2') is carried out, treatment can be uniformly performed without overlapping or missing a treatment field, as shown in FIG. 11.

According to the exemplary embodiment of the present invention, straight-line movement paths MZ and ML of the guide protrusion 330, which pass through the respective rotation guide grooves 134, may be formed in the shape of a zigzag (refer to FIG. 3). Alternatively, straight-line movement paths MZ and ML of the guide protrusion 330, which pass through the respective rotation guide grooves 134, may be formed in the shape of a continuous straight line.

For example, referring to FIG. 3, the linear guide groove 132 may include a first section guide groove 132a that is formed between any one pair that are adjacent to each other among the plurality of rotation guide grooves 134, and a second section guide groove 132b that is formed between another pair that are adjacent to each other among the plurality of rotation guide grooves 134 and disposed on a different line from a line where the first section guide groove 132a is disposed along the length direction of the probe 100.

For example, the plurality of rotation guide grooves 132 may include first, second, and third rotation guide grooves 132 that are disposed while continuously neighboring each other, and the first section guide groove 132a may be formed in a first section between the first and second rotation guide grooves 132 and the second section guide groove 132b may be formed in a second section that neighbors the first section. In this case, the first section guide groove 132a and the second section guide groove 132b may be disposed on different lines.

As described, the first section guide groove 132a and the second section guide groove 132b that form the linear guide groove 132 are disposed on different lines, and thus the guide protrusion 330 cannot enter the second section guide groove 132b right after moving along the first section guide groove 132a and can enter the second section guide groove 132b only after passing through the rotation guide groove 134. That is, the guide protrusion 330 moves along a zigzag movement path of the first section guide groove 132a→the rotation guide groove 134→the second section guide groove 132b.

When the straight line movement of the probe 100 with respect to the guide 300 is excessively performed due to carelessness or lack of experience of the operator, the treatment efficiency due to the electrode 200 is deteriorated, and a problem of damaging the patient may occur. However, in the exemplary embodiment of the present invention, the straight line movement of the probe 100 relative to the guide 300 is performed stepwise by the separation distance between each rotation guide groove 134, and thus an advantageous effect of improving treatment efficiency and improving treatment safety and convenience can be obtained.

Figure 7:
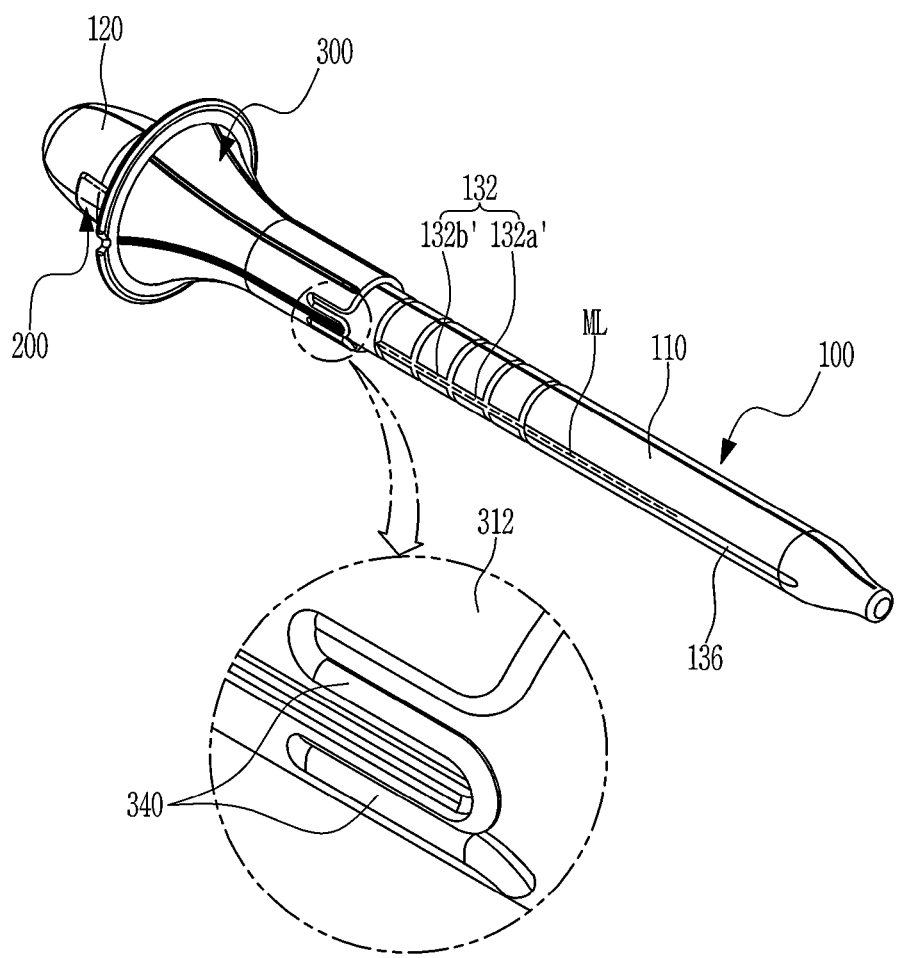
FIG. 7 and FIG. 8 are provided for description of a cut-out portion of the submucosa treating apparatus according to the exemplary embodiment of the present invention.

As another example, referring to FIG. 7, the linear guide groove 132 may include a first section guide groove 132a' formed between any one pair that are adjacent to each other among the plurality of rotation guide grooves 134, and a second section guide groove 132b' that is formed between another pair that are adjacent to each other among the plurality of rotation guide grooves 134 and disposed on a different line from a line where the first section guide groove 132a' is disposed along the length direction of the probe 100.

As described, the first section guide groove 132a and the second section guide groove 132b that form the linear guide groove 132 are disposed on the same line, and thus the guide protrusion 330 can directly enter the second section guide groove 132b after moving along the first section guide groove 132a'. That is, the guide protrusion 330 moves along a straight-line movement path of the first section guide groove 132a'→the rotation guide groove 134→the second section guide groove 132b'.

Depending on the patient's condition, treatment with the electrode 200 may be difficult in certain areas of mucosa (e.g., wounds). Thus, in the exemplary embodiment of the present invention, the straight line movement of the probe 100 with respect to the guide 300 is continuously performed in the first section guide groove 132a' and the second section guide groove 132b' and thus it is possible to pass the electrode 200 more quickly in an area where treatment is unnecessary, thereby obtaining an advantageous effect of shortening the treatment time and increasing the treatment efficiency.

In addition, referring to FIG. 2, in the exemplary embodiment of the present invention, a restraining groove 138 where the guide protrusion 330 is accommodated and temporarily restrained may be formed in the guide groove 130.

For example, as shown in the enlarged view of FIG. 1, the restraining groove 138 may be formed in a hemispherical form in which the guide protrusion 330 can be selectively accommodated or drawn out.

Accordingly, when the guide protrusion 330 is accommodated in the restraining groove 138, the alignment state of the guide protrusion 330 is restrained and the position is maintained unless the external force (operator's manipulation force) is applied to the probe 100. On the other hand, when the external force such as operator's manipulation force is applied to the probe 100 while the guide protrusion 330 is accommodated in the restraining groove 138, the guide protrusion 330 comes out of the restraining groove 138.

As described, since the restraining groove 138 is formed in the guide groove 130, when the probe 100 is operated, the operator can feel a feeling of manipulation, and can visually recognize (e.g., recognize the position of the electrode 200 with reference to the referential position mark 302) and also tactilely recognize (sound and impact felt when the guide protrusion 330 is accommodated or drawn out to the restraining groove 138) the position of the electrode 200 with respect to mucosa.

For example, as shown in FIG. 2, the restraining groove 138 may be provided in plural, and thus may be formed in the rotation guide groove 134 spaced apart along the circumferential direction of the probe 100. In this case, the restraining groove 138 may be formed at equal intervals along the circumferential direction of the probe 100. In addition, the restraining groove 138 may be spaced apart by the length (L2 of FIG. 3) of the electrode 200 along the circumferential direction of the probe 100. That is, the restraining groove 138 may be formed to be spaced apart from the length of the electrode 200 along the circumferential direction of the probe 100 (L2 of FIG. 3) as a separation pitch (P1 of FIG. 11).

As described, the plurality of restraining grooves 138 are formed in the rotation guide groove 134 while using the length L2 of the electrode 200 along the circumferential direction of the probe 100 as the separation pitch P1, and the guide protrusion 330 passes through each restraining groove 138 stepwise such that when the vaginal mucosa is treated along the circumferential direction (e.g., H1→H2→H3→H4), treatment can be performed uniformly without overlapping or missing a treatment field, as shown in FIG. 11. In addition, it is also possible to intentionally overlap or omit the treatment of a specific area using the sense of manipulation sensed through the restraining groove 138.

More specifically, when the plurality of restraining grooves 138 are formed at equal intervals along the circumferential direction of the rotation guide groove 134 and the probe 100 is manipulated by rotating, the operator is able to determine the number of times of rotation of the electrode 200 inside the vaginal mucosa by the manipulation feeling that occurs whenever the guide protrusion 330 passes through the restraining groove 138.

For example, the plurality of restraining grooves 138 may be formed at 60° intervals along the circumferential direction of the rotation guide groove 134, and it can be seen whether the electrode 200 rotates by 60° inside the vaginal mucosa by the manipulation feeling that occurs when the guide protrusion 330 passes the restraining groove 138 once by the rotation operation of the probe 100.

Figure 8:
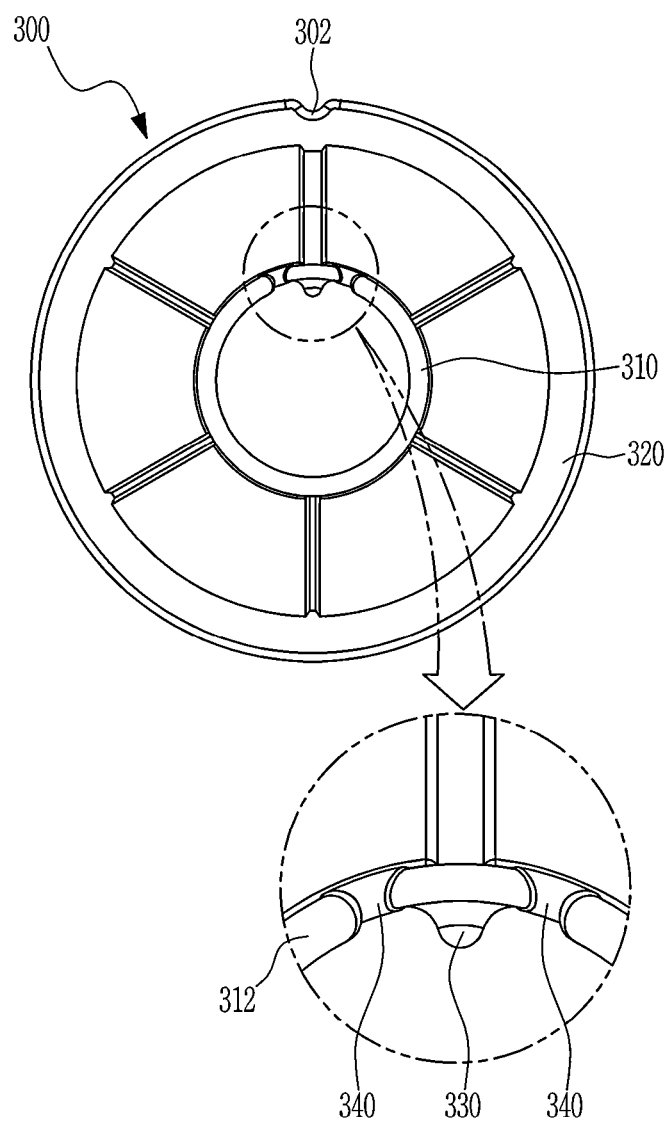

Meanwhile, referring to FIG. 7 and FIG. 8, a cut-out portion 340 is formed at the periphery of the guide protrusion 330 in the guide 300, and a cantilever structure of which a fixed end is formed at one end and a free end is formed at the other end is formed by the cut-out portion 340 such that the guide protrusion 330 can be formed in the cantilever structure.

That is, the guide protrusion 330 may be disposed to the free end of the cantilever structure formed between the guide 300 and a pair of cut-out portions 340.

For example, a pair of cut-out portions 340 formed in the length direction of the probe 100 and spaced apart from each other in the circumferential direction of the probe 100 may be formed at the end of the body portion 310. Depending on cases, the cut-out portion 340 can also be formed in other directions. In this case, the guide protrusion 330 may be disposed to the free end of the cantilever structure formed by the pair of cut-out portions 340.

As described, smooth movement of the guide protrusion 330 in the guide groove 130 is ensured by allowing the guide protrusion 330 to flow elastically through the cantilever structure, and the restraining and releasing of the guide protrusion 330 with respect to the restraining groove 138 can be carried out more naturally.

In addition, referring to FIG. 3, a position-mark 140 that indicates the position of the probe 100 with respect to the guide 300 may be formed on the probe 100.

Here, the position of the probe 100 with respect to the guide 300 is defined to include both rotation position and straight line movement position of the probe 100 with respect to the guide 300.

For example, the position-mark 140 may be formed at an outer surface of the probe 100 along the length direction of the probe 100, and the rotation position and the straight line movement position of the electrode 200 for the mucosa can be controlled with reference to the position of the position-mark 140. For example, the rotation position of the electrode 200 can be determined by comparing the referential position mark 302 and the position-mark 140 formed in the guide 300.

The position-mark 140 may be marked or painted in the form of a dot or line on the outer surface of the probe 100. In another form, the position-mark may be formed in a protrusion shape or a recessed groove shape on the outer surface of the probe.

Figure 4:
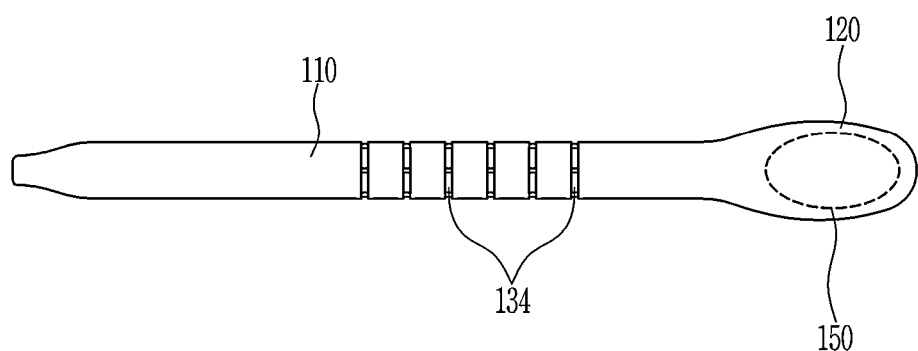

In addition, referring to FIG. 4, a weight body 150 may be provided inside the head portion 120.

Here, the weight body 150 may include a weight built into the head portion 120 to increase the weight of the head portion 120 in the probe 100.

As described above, the alignment stability of the probe 100 is increased while the head portion 120 is inserted inside the body by increasing the weight of the head portion 120 in the probe 100 through the weight body 150, and the operation of the probe 100 can be more conveniently carried out. When the weight of the head portion 120 is the smallest in the probe 100, the head portion 120 may be easily displaced outside the body while being inserted into the body, and operability may be deteriorated.

The submucosa treating apparatus 10 according to the exemplary embodiment of the present invention may include a controller 230 that controls power supply to the electrode 200 when the electrode 200 is positioned at a predetermined non-target site of mucosa.

Here, controlling the power supply to the electrode 200 is defined to include all of blocking or reducing the power supply to the electrode 200.

For example, when the treatment site is vaginal mucosa, the non-target site may be the urethra, and the controller 230 may stop or reduce the power supply to the electrode 200 when the electrode 200 is positioned at the non-target site.

As described, when the electrode 200 is positioned in the urethral region, an advantageous effect of preventing thermal burns or tissue stenosis in the urethral region can be obtained by stopping or reducing the power supply to the electrode 200.

For example, the controller 230 may stop the power supply to the electrode 200 when the position of the electrode 200 is detected to be between the 11 o'clock (11:00) direction and the 1 o'clock (13:00) direction with reference to the 12 o'clock direction (12:00) at which the urethra is positioned along the circumferential direction of the vagina.

As described, according to the exemplary embodiment of the present invention, excluding the urethral region positioned at the 12 o'clock direction (12:00), deep heat is applied to the blood vessels of the vaginal submucosa by electrical signals to normalize the abnormal overgrowth of the blood vessels, and thus it is possible to obtain the effect of maintaining the contractility of the vaginal tissue and improving elasticity.

Figure 14:
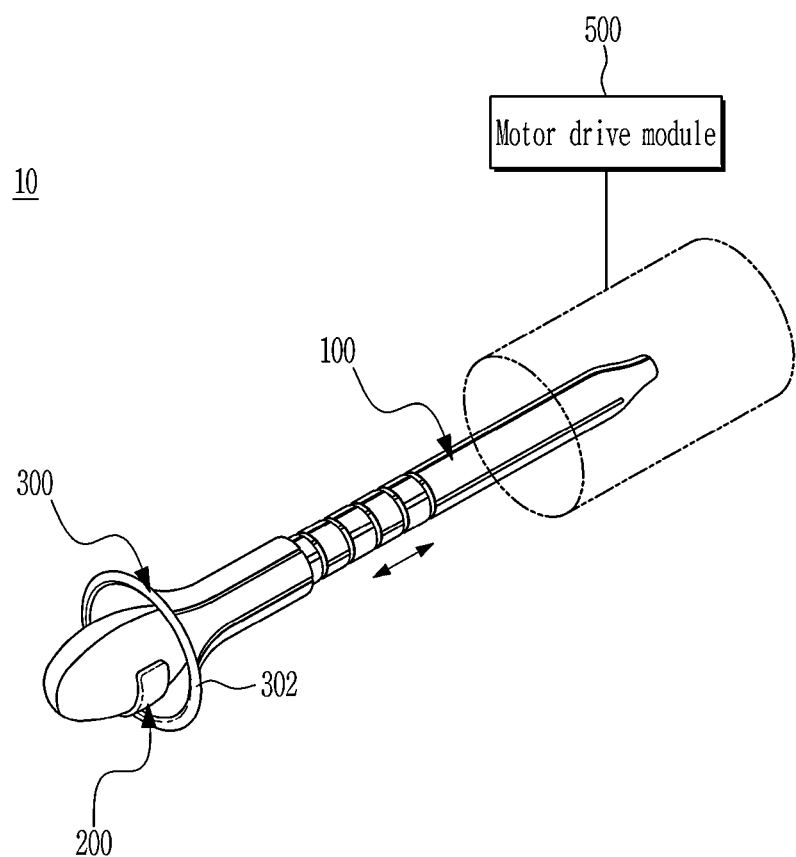
FIG. 14 is provided for description of a motor drive module of the submucosa treating apparatus according to the exemplary embodiment of the present invention.

Referring to FIG. 14, in the exemplary embodiment of the present invention, a motor drive module 500 may be further included to automatically rotate as a user pre-sets after rotation of the probe that includes the electrode.

Although it is not illustrated, according to another exemplary embodiment of the present invention, the electrode 200 may be formed of a plurality of electrode modules, and the plurality of electrode modules may be positioned on the entire surface of the head portion 120 of the probe 100. Thus, electrical signal conduction can be sequentially carried out to each electrode module such that the entire area to be treated can be uniformly treated without direct movement of the probe 100.

For reference, in the above-described exemplary embodiment of the present invention, the submucosa treating apparatus 10 is exemplarily used for the purpose of treatment of the urethral region, but this is not restrictive, and it is also possible to intensively treat the 11-1 o'clock direction near the urethra for the purpose of any treatment of the urethral region (e.g., urinary incontinence treatment). In this case, in the treatment of the urethral region, the electrical signal by the electrode can be controlled to be adjusted with suitable intensity and applied.

While this invention has been described in connection with what is presently considered to be practical exemplary embodiments, it is to be understood that the invention is not limited to the disclosed embodiments. On the contrary, it is intended to cover various modifications and equivalent arrangements included within the scope of the appended claims.

DESCRIPTION OF SYMBOLS

| | |
|---|---|
| 10: submucosa treating apparatus | 100: probe |
| 110: load portion | 120: head portion |
| 130: guide groove | 132: linear guide groove |
| 132a, 132a': first section guide groove | |
| 132b, 132b': second section guide groove | |
| 134: rotation guide groove | 136: ingress groove |
| 138: restraining groove | 140: position-mark |
| 150: weight body | 200: electrode |
| 202: electrode pad | 204: electrode protrusion |
| 210: coating layer | 230: controller |
| 300: guide | 302: referentia position mark |
| 310: body portion | 312: first accommodation hole |
| 320: expanded portion | 322: second accommodation hole |
| 330: guide protrusion | 340: cut-out portion |
| 400: guide portion | 500: motor drive module |

The invention claimed is:

1. A submucosa treating apparatus comprising:
a probe for approaching mucosa of a treatment field;
an electrode provided in the probe having a quadrangle form, and applying an electrical signal to blood vessels of submucosa; and
a guide for guiding a position of the electrode with respect to the mucosa, and
wherein the probe is movably accommodated in the guide,
wherein a position of the guide with respect to the mucosa is fixed, and the probe is fully rotatable and straightly movable with respect to the guide,
wherein the guide comprises a referential position mark, and guides a rotation position of the electrode with respect to the mucosa with reference to the referential position mark, and
wherein the submucosa treating apparatus further comprises a guide portion for guiding rotation and straight-line movement of the probe with respect to the guide,
wherein the guide portion comprises
a guide groove formed in the probe, and
a guide protrusion formed in the guide and sliding along the guide groove,
wherein the guide groove comprises:
a linear guide groove that extends along a length direction of the probe at an outer surface of the probe; and
a plurality of rotation guide grooves that communicate with the linear guide groove and are spaced apart from each other along the length direction of the probe, and
wherein each of the plurality of rotation guide grooves extends along a circumferential direction of the probe at the outer surface of the probe,
wherein the plurality of rotation guide grooves are spaced apart from each other by a separation pitch along the length direction of the probe,
wherein the electrode has a horizontal length and a vertical length, the horizontal length being parallel to the length direction of the probe,
wherein the separation pitch is equal to the entire horizontal length of the electrode.

2. The submucosa treating apparatus of claim 1, wherein the guide comprises:
a body portion where a first accommodation hole in which the probe is rotatably accommodated is formed; and
an expanded portion that communicates with the first accommodation hole and where the probe is rotatably accommodated, and is formed while integrally expanding from the body portion.

3. The submucosa treating apparatus of claim 1, wherein the plurality of rotation guide grooves comprise first, second, and third rotation guide grooves that continuously neighbor each other, and
the linear guide groove comprises
a first section guide groove formed between the first rotation guide groove and the second rotation guide groove, and
a second section guide groove formed between the second rotation guide groove and the third rotation guide groove, and disposed on a line different from the line where the first section guide groove is disposed along the length direction of the probe.

4. The submucosa treating apparatus of claim 1, comprising a plurality of restraining grooves formed in the guide groove, and
wherein the guide protrusion is accommodated while being position-fixed in the plurality of restraining grooves.

5. The submucosa treating apparatus of claim 4, wherein the plurality of restraining grooves are formed in the rotation guide groove and spaced apart from each other along a circumferential direction of the probe.

6. The submucosa treating apparatus of claim 5, wherein the plurality of restraining grooves are spaced from each other by as much as a length of the electrode along the circumferential direction of the probe.

7. The submucosa treating apparatus of claim 4, wherein a pair of cut-out portions are formed along the length direction of the probe at an end of the body portion, and are distanced from each other along the circumferential direction of the probe, and
the guide protrusion is disposed at a free end of a cantilever structure formed by the pair of cut-out portions.

8. The submucosa treating apparatus of claim 1, comprising a position-mark formed in the probe, and indicating a position of the probe with respect to the guide.

9. The submucosa treating apparatus of claim 1, wherein
the electrode is mounted to partially cover an outer surface of the head portion while having a size smaller than the head portion, and
the outer surface of the electrode is curved such that the electrical signal is emitted in a radial shape through the curved surface of the electrode.

10. The submucosa treating apparatus of claim 1, wherein the electrode comprises:
an electrode pad attached to the probe; and
an electrode protrusion protruding from an outer surface of the electrode pad.

11. The submucosa treating apparatus of claim 1, comprising a coating layer formed at the outer surface of the electrode, the coating layer suppressing thermal conduction to the mucosa from the electrode.

12. The submucosa treating apparatus of claim 1, wherein the electrical signal is a pulse signal that is iteratively conducted while having at least one delay time.

* * * * *